United States Patent

Kauvar et al.

Patent Number: 5,908,919
Date of Patent: Jun. 1, 1999

[54] URETHANE MEDIATED, GST SPECIFIC MOLECULAR RELEASE SYSTEMS

[75] Inventors: Lawrence M. Kauvar, San Francisco; Matthew H. Lyttle, Point Reyes Station; Apparao Satyam, Fremont, all of Calif.

[73] Assignee: Terrapin Technologies, South San Francisco, Calif.

[21] Appl. No.: 08/476,119

[22] Filed: Jun. 7, 1995

Related U.S. Application Data

[63] Continuation-in-part of application No. 08/309,005, Sep. 19, 1994, Pat. No. 5,556,942, which is a continuation-in-part of application No. 08/130,736, Oct. 1, 1993, Pat. No. 5,545,621.

[51] Int. Cl.$^6$ .............. C07K 5/08; C07K 5/023; A61K 38/00; A61K 38/06

[52] U.S. Cl. ............ 530/331; 530/330; 530/332; 530/333; 514/18

[58] Field of Search .................. 530/331, 332, 530/333, 330; 514/18

[56] References Cited

U.S. PATENT DOCUMENTS

| | | |
|---|---|---|
| 4,851,388 | 7/1989 | Bright. |
| 4,963,263 | 10/1990 | Kauvar. |
| 5,133,866 | 7/1992 | Kauvar. |
| 5,204,241 | 4/1993 | Pero. |
| 5,430,045 | 7/1995 | Goldberg et al.. |
| 5,545,621 | 8/1996 | Kauvar et al. ............... 514/18 |
| 5,556,942 | 9/1996 | Kauvar et al. ............... 530/331 |
| 5,648,506 | 7/1997 | Desai et al. ............... 549/510 |

FOREIGN PATENT DOCUMENTS

| | | |
|---|---|---|
| 163550 | 12/1985 | European Pat. Off.. |
| 420121 | 4/1991 | European Pat. Off.. |
| WO 86/00991 | 7/1985 | WIPO. |
| WO 86/06487 | 11/1986 | WIPO. |
| WO 90/12088 | 4/1990 | WIPO. |
| WO 91/17240 | 5/1991 | WIPO. |
| WO 92/19767 | 4/1992 | WIPO. |
| WO 95/08563 | 3/1995 | WIPO. |
| WO 95/09866 | 4/1995 | WIPO. |

OTHER PUBLICATIONS

Adang, et al., "The Glutathione–Binding Site in Glutathione S–Transferases, Investigation of the cysteinyl, glycyl and y–glutamyl domains" *Biochem. J.* 269:47–54 (1990).

Borch et al., "Synthesis and Antitumor Properties of Activated Cyclophosphamide Analogues," *J Med Chem* (1991) 34:3044–3052.

Borch et al., "Synthesis, Activation and Cytotoxicity of Aldophosphamide Analogues," *J. Med Chem* (1991) 34:3052–3058.

(List continued on next page.)

*Primary Examiner*—Marian C. Knode
*Assistant Examiner*—Datquan Lee
*Attorney, Agent, or Firm*—Kate H. Murashige; Morrison & Foerster, LLP

[57] ABSTRACT

Compounds of the formula

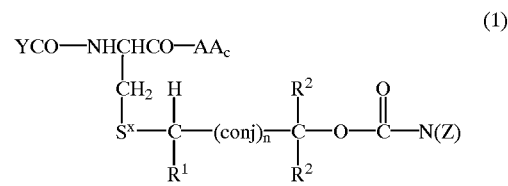

(1)

or of the formula

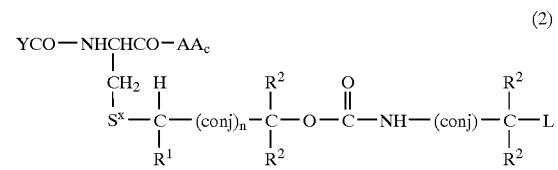

(2)

or the amides, esters or salts thereof, wherein:

$S^x$ is S=O, O=S=O, S=NH, HN=S=O, Se=O, O=Se=O, Se=NH, HN=Se=O, $S^+R^3$ wherein $R^3$ is alkyl (1-6C) or O—C=O or HN—C=O;

each R of $R^1$, and $R^2$ is independently H or a noninterfering substituent;

wherein (conj) represents a conjugated system capable of transmitting electrons;

n is 0 or 1;

YCO is selected from the group consisting of γ-Glu, γ-Glu-Gly, Glu, Glu-Gly, βAsp, β-Asp-Gly, Asp and Asp-Gly;

$AA_C$ is an amino acid linked through a peptide bond to the remainder of said compound of Formula 1; and N(Z) represents a reduced nitrogen-containing leaving group and L represents an electron-withdrawing leaving group, are useful as prodrugs and to generate active components released by the activity of glutathione S-transferase.

33 Claims, No Drawings

OTHER PUBLICATIONS

Borch et al., "In Situ Preparation and Fate of cis–4–Hydroxycyclophosphamide and Aldophosphamid: $^1$H and $^{31}$P NMR Evidence for Equilibration of cis– and trans–4–Hydroxycyclophosphamide with Aldophosphamide and Its Hydrate in Aqueous Solution," *J Med Chem* (1984) 27:490–494.

Borch et al., "The Mechanism of Activation of 4–Hydroxycyclophosphamide," *J Med Chem* (1987) 30:427–431.

Campling, et al. "Do glutathione and related enzymes play a role in drug resistance in small cell lung Cancer cell lines?" *Br. J. Cancer* 68:327–335 (1993).

Castro, et al., "Differences Among Human Tumor Cells in the Expression of Glutathione Transferases and Other Glutathione–Linked Enzymes" *Carcinogenesis* Oxford University Press, 1569–1576 (1990).

Chatterjee, et al., "Idiotypic antibody immunotherapy of cancer" *Cancer Immunol. Immunotherap.* 38:75–82 (1994).

Dermer "Another Anniversary for the War on Cancer" *Biotechnology* 12:320 (1994).

Fenselau, C. and P.B.W. Smith, "High–Performance tandem mass spectrometry in metabolism studies", *Xenobiotica* 22(9/10):1207–1219 (1992).

Flatgaard et al., "Isozyme specificity of novel glutathione–S–transferase inhibitors" *Cancer Res.* 33:63–70 (1993).

Held, et al., "Effect of Dimethyl Fumarate on the Radiation Sensitivity of Mammalian Cells in Vitro" *Radiation Research* 115: 495–502 (1988).

Houghton Mifflin Company *Webster's II New Riverside University Dictionary*, 849 (1988).

Kauvar, et al., "Paralog Chromatography" *Biotechniques* 8:204–209 (1990).

Ketterer, B. et al., "Glutathione Conjugation : Mechanisms and Biological Significance", Sies, H., et al., eds., (1988) Academic Press, London, pp. 74–137.

Lyttle, M.H. et al., "Glutathione–S–Transferase Activates Novel Alkylating Agents" *J Med Chem* 37(10):1501–1507 (1994).

Mannervik, B. et al., "Glutathione Transferases—Structure and Catalytic Activity" *CRC Crt Rev Biochemistry* (1988) 23:283–355.

Mannervik, et al. "Identification of Three Classes of Cytosolic Glutathione Transferase Common to Several Mammalian Species: Correlation Between Structural Data and Enzymatic Properties" *Proc. Natl. Acad. Sci. USA*, 82:7202–7206 (1985).

Merck Manual, Fifteenth Edition, Merck & Co., Rahway, NJ (1987) pp. 1120–1121.

Morris, D., "Synthesis of the α– and γ–Isomers of Glutamylcystinylvaline", *Biochem J.* (1960) 76:349–353.

O'Dwyer et al., "Depletion of Glutathione in Normal and Malignant Human Cells In Vivo by Buthionine Sulfoximine: Clinical and Biochemical Results" *J NCI* 84:264–267 (1992).

O'Dwyer et al., "Phase I Study of Thiotepa in Combination with the Glutathione Transferase Inhibitor Ethacrynic Acid" *Cancer Res.* 51:6059–.

Principato, G.B., et al., "Effects of Some S–Blocked Glutathione Derivatives on the Prevalent Glyoxalase II (a Form) of Rat Liver, Enzyme" *Biochem J.* (1989) 41:175–180.

Puchalski, R.B. et al., "Expression of Recombinant Glutathione S–Transferase π, Ya, or Yb$_1$ Confers Resistance to Alkylating Agents" *Proc Natl Acad Sci USA* (1990) 87:2443–2447.

Reinemar, P., et al., "Three–dimensional Structure of Class π Glutathione S–Transferase from Human Placenta in Complex with S–Hexylglutathione at 2.8 A Resolution"; *J Mol Biol* (1992) 213:214–226.

Ricci, et al. "Detection of Glutathione Transferase Activity on Polyacrylamide Gels" *Analytical Biochemistry* 143, 226–230 (1984).

Ripple, et al., "Characteristics of the Glutathione/Glutathione–S–Transferase Detoxification System in Melphalan Resistant Human Prostate Cancer Cells" *J. Urology* 150:209–214 (1993).

Satou, Patent Abstracts of Japan; JP–A–60–199–384, vol. 10, No. 56; Glutathione S–transferase.

Schisselbauer, J.C., et al., "Characterization of Glutathione S–Transferase Expression in Lymphocytes from Chronic Lymphocytic Leukemia Patients"; *Cancer Res* (1990) 50:3562–2568.

Sharer et al., "Formation, stability and rearrangements of the gluthathione conjugates of butadiene monoxide; evidence for the formation of stable surfurane intermediates", *Chem. Res. Toxicol.* (1991), 4(4):430–6 CODEN: CRTOEC; ISSN:0893–228X, 1991, pp. 434–435.

Sheh, et al. "Synthesis of Cyclic Peptide Homologs of Glutathione as Potential Antitumor Agents" Int. *J. Peptide protein Res.* 35:55–62 (1990).

Smith, et al. "Denitrosation of 1,3–Bis(2–chloroethyl)–1–nitrosourea by Class Mu glutathione Transferases and Its Role in Cellular Resistance in Rat Brain Tumor Cells" *Cancer Research* 49:2621–2625 (1989).

Takeo, et al. "Binding Constants of Dextrans and Isomaltose Oligosaccharides to Dextran–Specific Myeloma Proteins Determined by Affinity Electrophoresis" *J. Immunol..* 121:2305–2310 (1978).

Tew, et al. "Ethacrynic Acid and Piriprost as Engancers of Cytotoxicity in Drug Resistant and Sensitive Cell Lines" *Cancer Research* 48:3622–3625 (1988).

van Bladeren, et al., "The Inhibition of Glutathione S–Transferases: Mechanisms, Toxic Consequences and Therapeutic Benefits" *Pharmac. Ther.* 51:35–46 (1991).

Vos. et al. "Differential Induction of Rat Hepatic Glutathion S–Transferase Isoenzymes by Hexachlorobenzene and Benzyl Isothiocyanate" *Biochemical Pharmacology* No.37(6):1077–1082 (1988).

Waxman "Gluthathione S–Transferases Role in Alkylating Agent Resistance and Possible target for Modulation Chemotherapy—A Review" *Cancer Research* 50:6449–6454 (1990).

Wiencke et al. "Human Glutathione S–Transferase Deficiency as a Market of Susceptibility to Expoxide–Induced Cytogenetic Damage" *Cancer Research* 50:1585–1590 (1990).

Ciaccio P.J. et al. "Modulation of Detoxification Gene Expression in Human Colon HT129 Cells by Glutathione–S–Transferase Inhibitors" *Molecular Pharmacology* 48:639–647 (1995).

Annual Meeting of the Canadian Society for Clinical Investigation and the Royal College of Physicians and Surgeons of Canda, Montreal, Quebec, Canada, Sep. 13–17, 1995, "Clinical and Investigative Medicine," vol. 18 (4 Suppl.) (1995), Cournoyer D. et al.

Morgan A. S. et al. "Isozyme–specific Glutathione S–Transferase Inhibitors Potentiate Drug Sensitivity in Cultured Human Tumor Cell Lines," *Cancer Chemother. Pharmacol.* 37:363–370 (1996).

URETHANE MEDIATED, GST SPECIFIC MOLECULAR RELEASE SYSTEMS

This application is a continuation-in-part of U.S. Ser. No. 08/309,005 filed Sep. 19, 1994 now U.S. Pat. No. 5,556,942, issued on Sep. 17, 1996, which is a continuation-in-part of U.S. Ser. No. 08/130,736 filed Oct. 1, 1993 now U.S. Pat. No. 5,545,621, issued Aug. 13, 1996. This application also claims priority from PCT/US94/11109 filed Sep. 30, 1994. The contents of these applications are incorporated herein by reference.

TECHNICAL FIELD

The invention relates to compounds capable of releasing useful entities wherein the release is catalyzed by glutathione S-transferase (GST). More specifically, the invention concerns such compounds wherein the release is mediated by electron donation to the leaving group through a urethane linkage.

BACKGROUND ART

Electron transit through a urethane linkage has been utilized to construct prodrugs by Senter, P. D. et al., *J Org Chem* (1990), 55:2975. In this work, the reduction of a disulfide bridging two phenyl moieties was used to mediate the release of either nitroaniline or mitomycin C, wherein the amino group of the substance released was part of a urethane linkage para to the disulfide on one of the phenyl moieties. The reduction released electrons through the phenyl moiety to decompose the urethane. This provided the released nitroaniline or mitomycin C, and $CO_2$ as a by-product.

In addition, Nicolaou, K. C. et al., *Angew Chem Int Ed Engl* (1991) 30:1032 describe the release of a dynemycin A analog wherein the amino group of the dynemycin A analog was included as part of a urethane linkage to the moiety $\phi$—$SO_2CH_2OC(O)$—N. Neither of these prodrug type molecules is enzyme regulated.

PCT/US1994/11109 referenced and incorporated above was published Apr. 13, 1995 as WO95/09866. This published application describes a set of glutathione S-transferase activated compounds wherein the release of a desired leaving group is actuated by abstraction of a hydrogen ion $\alpha$ to the cysteinyl sulfur atom in a glutathione analog. The nature of the glutathione analog will determine which isoenzyme of GST will be the most effective in activating the release of the leaving group. Also disclosed in WO95/09866 is the inclusion of a urethane linkage within the leaving group, so that $CO_2$ is released when the leaving group is released as well.

The use of a conjugated $\pi$ system to participate in the transfer of electrons from a relevant portion of a prodrug to the group released is also described by Papanastassiou, Z. B. et al., *Experientia* (1968) 24:325 and Tercel, M. et al., *J Med Chem* (1993) 36:2578, as well as in the PCT reference described above.

It has now been found that the enzyme specificity conferred by the nature of glutathione analogs can be coupled with the electron release mechanisms associated with the urethane linkage to provide a new class of effective prodrugs for a variety of nitrogen-containing pharmaceuticals as well as more generally a release mechanism for any moiety containing reduced nitrogen. In addition, by taking advantage of the ability to move electrons through a conjugated system, the urethane-mediated linkage can be employed to release moieties which do not contain reduced nitrogen as part of the urethane linkage per se.

DISCLOSURE OF THE INVENTION

The invention relates to a new class of GST-activated compounds capable of releasing desired moieties by electron transfer through a urethane linkage, with concomitant release of $CO_2$, optionally through coupling to a conjugated system. These compounds have the advantage of GST-regulated specificity, the equilibrium-driving properties associated with $CO_2$ release, and general applicability to release of electron withdrawing leaving groups. The compounds of the invention are therefore useful as prodrugs as well as laboratory reagents.

Thus, in one aspect, the invention is directed to a compound of the formula

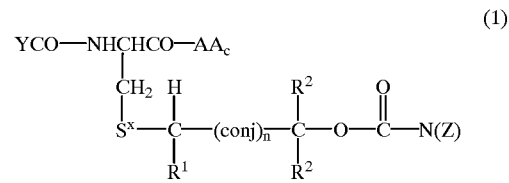

(1)

or the amides, esters or salts thereof, wherein:

$S^x$ is S=O, O=S=O, S=NH, HN=S=O, Se=O, O=Se=O, Se=NH, HN=Se=O, $S^+R^3$ wherein $R^3$ is alkyl (1–6C) or O—C=O or HN—C=O;

each R of $R^1$, and $R^2$ is independently H or a noninterfering substituent;

wherein (conj) represents a conjugated system capable of transmitting electrons;

n is 0 or 1;

YCO is selected from the group consisting of γ-Glu, γ-Glu-Gly, Glu, Glu-Gly, βAsp, β-Asp-Gly, Asp and Asp-Gly;

$AA_C$ is an amino acid linked through a peptide bond to the remainder of said compound of Formula 1; and N(Z) represents a reduced nitrogen-containing leaving group.

The invention also relates to a compound of the formula

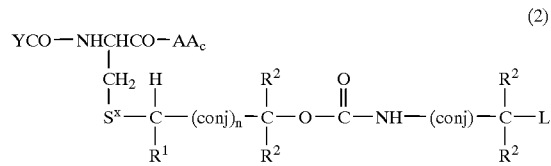

(2)

wherein $S^x$, $R^1$, $R^2$, YCO, conj, n, and $AA_C$ are defined as above for Formula 1; and L represents an electron withdrawing leaving group.

In other aspects, the invention is directed to methods of synthesizing the compounds of Formulas 1 and 2, to pharmaceutical compositions containing these compounds, and to methods to impair or otherwise affect tumor cells or other targets by administering the compounds of Formulas 1 or 2 in contexts where the prodrugs are selectively cleaved by the targets to release N(Z) or L, which is typically a cytotoxic agent.

In still other aspects, the invention is directed to methods selectively to treat tumor cells or other target cells with characterized GST contents by selectively administering the prodrugs of the invention that are sensitive to cleavage with a GST that shows an elevated level in the target cells.

MODES OF CARRYING OUT THE INVENTION

The compounds of the invention are prodrugs which can be used selectively to target tissues having GST complements which are elevated or which contain isoenzymes peculiar in specificity to the prodrug provided. Depending on the nature of YCO and $AA_C$, these compounds are differentially activated by GST enzymes of the $\mu$, $\pi$ and $\alpha$ classes. These prodrugs, in addition to being selective for cells with elevated GST complements per se, can be used in a finely tuned protocol to target cells which have elevated levels of a particular isoenzyme of the GST group.

In an additional use, the compounds of Formulas 1 and 2 can be used as analytical reagents for GST activity by employing as "L" or "N(Z)" an indicator group which is detectable when liberated from the compounds of Formulas 1 or 2. Such a reagent is suitable for determining the concentration of GST of known substrate specificity, or analyzing the specificity of particular GSTs by varying the glutathione analog component of the compounds of Formulas 1 or 2.

COMPOUNDS OF THE INVENTION

The compounds of the invention are comprised of a tripeptide which is glutathione or an analog thereof coupled to a leaving group through a molecular system which permits release of the leaving group N(Z) or L when the compounds of Formulas 1 or 2 are treated with the appropriate GST. $CO_2$ will also be released. The release of the leaving group occurs through a "β-elimination"—i.e., the removal of the proton on the carbon α to the electron-poor oxidized carbon, sulfur or selenium releases electrons which are ultimately absorbed by the leaving group and result in its release. This can be shown schematically as follows:

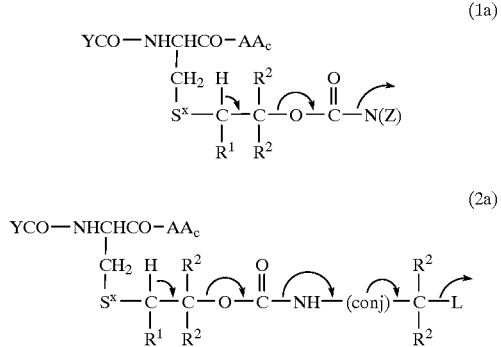

The electron pair can be released to the leaving group through liberation of $CO_2$ directly through β-elimination as shown above or through a system of conjugation represented by (conj), when n is 1 in Formula 1 or 2.

The substituents $R^1$ and $R^2$ play no direct part in the release of substituent N(Z) or L and simply must be noninterfering substituents. The rate of β-elimination can be controlled by the nature of these R groups; by choosing electron withdrawing or electron donating substituents the rate of elimination can be accelerated or decreased. Suitable substituents for $R^1$ and $R^2$ include H, substituted or unsubstituted alkyl (1–6C) substituted or unsubstituted aryl (6–12C), substituted or unsubstituted aryl alkyl (7–12C), cyano, halo, substituted or unsubstituted alkoxy (1–6C), substituted or unsubstituted aryloxy (6–12C) or substituted or unsubstituted arylalkyloxy (7–12C).

Alkyl, aryl, and arylalkyl have their conventional meanings; alkyl groups are straight, branched chain or cyclic saturated hydrocarbon moieties such as methyl, tert-butyl, cyclohexyl, and the like. Aryl groups include aromatic systems such as phenyl, naphthyl, pyridyl and the like. Arylalkyl substituents contain an aryl moiety coupled to the remainder of the molecule through an alkylene moiety. Such groups include, most commonly benzyl, phenylethyl, 2-pyridylethyl, and the like.

Suitable substituents in the substituted forms include halo, SR, OR, and $NR_2$ wherein R is H or lower alkyl (1–4C).

Preferred embodiments for $R^1$ and $R^2$ independently are H, lower alkyl (1–4C) and phenyl. In particularly preferred embodiments, $R^1$ is H or phenyl, all $R^2$ are H and n=0. However, any noninterfering substituents may be used as $R^1$ and $R^2$. These substituents are independently embodied.

The embodiments of YCO and $—AA_C$ determine the nature of the glutathione-like tripeptide. A preferred embodiment is that wherein YCO is γ-glutamic and $AA_C$ is glycine, phenylglycine, β-alanine, alanine or phenylalanine, resulting in the tripeptide glutathione or a close analog. However, alternative embodiments of YCO include β-Asp, Glu, Asp, γ-GluGly, β-AspGly, GluGly and AspGly. Alternative embodiments of $AA_C$ include, along with the preferred glycine, phenylglycine, β-alanine, alanine, and unsubstituted phenylalanine: valine, 4-aminobutyric acid, aspartic, substituted phenylglycine, histidine, tryptophan, tyrosine, and substituted phenylalanine. Suitable phenylalanine and phenylglycine substituents are as described above for the substituted forms of $R^1$ and $R^2$.

Suitable embodiments for L include those which generate drugs which may be cytotoxic to unwanted cells. Such drugs include the phosphoramide mustards, the phosphorodiamidate mustards, the chemotherapeutic agents adriamycin and daunorubicin, toxins such as ricin toxin or diphtheria toxin, antiinflammatory or steroid-based drugs and the like, and other metabolic modulators such as 2,3-di-t-butyl-4-hydroxyanisole. Preferred forms of the phosphorodiamidate mustards are $—OP(O)(N(CH_2CH_2Cl)_2)_2$, $—OP(O)(N(CH_2CH_2Br)_2)_2$, $—OP(O)(NHCH_2CH_2Cl)_2$ and $—OP(O)(NHCH_2CH_2Br)_2$. Any biologically active moiety, provided with an electron adsorbing linkage to the remainder of the compound so that "L" released by β-elimination may be used.

For embodiments of compounds of Formulas 1, the released moiety N(Z) includes, by definition, reduced nitrogen. Suitable released compounds then include the nitrogen mustards such as bis(2-chloroethyl)amine; uracil mustards wherein the bis (2-chloroethyl)amine is a substituent at the 5 position of the uracil ring and other mustards which include primary or secondary amines; various antibiotics which contain suitable amino groups to participate in the urethane linkage such as mitomycin C, actinomycin D, and the vinca alkaloids vincristine and vinblastine, and a dynemycin analog which subsequently follows a reaction path leading to a benzenoid diradical capable of effecting DNA inactivation by hydrogen atom abstraction.

As stated above, electron release can also be mediated through conjugated systems either to avoid the necessity for the inclusion of reduced nitrogen in the released moiety or simply to provide for electron flow or both. These conjugated systems may either be alkylene-based straight chain moieties such as $—CR=CR—$; $—CR=CR—CR=CR—$; $—CR=CR—CR=CR—CR=CR—$ and the like, or may be included in aliphatic or aromatic ring systems such as 1,3,cyclohexadiene wherein the ring system is included in the compound through bonds at the 1 and 4 positions, or benzene or other aromatic systems which are included through bonds to even numbers of carbons.

As shown in Formula 2, advantage may be taken of conjugated systems to liberate any moiety which can absorb electrons. For example, in an article by Mulcahy, R. T. et al., *J Med Chem* (1994) 37:1610, liberation of a phosphoramidate mustard was described. The phosphoramidate is coupled through a methylene linkage to a para-nitrobenzene moiety and the conjugate is reduced under hypoxic conditions present in some cells to liberate the phosphoramidate mustard OP(O)(N(CH$_2$CH$_2$Cl)$_2$)$_2$ leaving behind a para-phenylene monoamine. In the present invention compounds, similar liberation of the phosphoramidate mustard through the mediation of the para-nitrogen is effected by electron donation through the urethane moiety to the aromatic ring, again resulting in the para-phenylene monamine and phosphoramidate mustard.

Similarly, in a manner analogous to the known generation of the extremely cytotoxic nitrogen mustard mechlorethamine (Me—N(CH$_2$CH$_2$Cl)$_2$ by reduction of the quaternary amine coupled through a methylene linkage to ortho or para nitrobenzene, the β-elimination can again be used as a source of electrons through the mediation of a urethane linkage to generate the mechlorethamine and phenylene monamine byproduct. Non-GST mediated hypoxic release from ortho or para nitrobenzyl is described by Papanastassiou, Z. B. et al., *Experientia* (1968) 24:325; Tercel, M. et al., *J Med Chem* (1993) 36:2578.

Preferred compounds of the invention are:

γ-Glutamyl-α-amino-β(2-ethyl, N,N-bis(2'-chloroethyl) carbamoyl)sulfonyl)propionyl glycine;

γ-Glutamyl-α-amino-β(2-ethyl, N,N-bis(2'-chloroethyl) carbamoyl)sulfonyl)propionyl phenyl glycine;

γ-Glutamyl-α-amino-β-((2-ethyl-(4-benzyloxy(N,N,N$^1$, N$^1$tetrakis(2-chloroethyl)phosphorodiamidate)) carbamido)sulfonyl)propionyl glycine;

γ-Glutamyl-α-amino-β-((2-ethyl-(4-benzyloxy(N,N,N$^1$, N$^1$tetrakis(2-chloroethyl)phosphorodiamidate)) carbamido)sulfonyl)propionyl phenyl glycine; and their diethyl esters.

In addition, indicator molecules such as p-nitrophenol can be used as leaving groups when the compounds of Formulas 1 or 2 is intended as a reagent.

The compounds of the invention may also be prepared in the forms of their esters or amides, or as their salts. The esters, amides or salts are formed with any or all carboxyl groups present in the molecule; hence, included in this group are monoesters, diesters, and, if applicable, triesters. Similarly, monoamides, diamides, or, if applicable, triamides are included.

The esters or amides may be alkyl (1–6C), alkenyl (1–6C) or arylalkyl (7–12C). Alkyl esters of the free carboxyls are esters of the straight- and branched-chain alkyl alcohols (1–6C) such as methanol, ethanol, isopropanol, t-butanol, n-hexanol and the like. Suitable alkyl (1–6C) amides are those of primary straight- or branched-chain alkyl amines, such as methylamine, ethylamine, n-propylamine, isopentylamine, and isohexylamine. Alkenyl esters are similar, but contain at least one double bond. Arylalkyl is as defined above. The alcohols or amines may also carry noninterfering substituents such as halo, alkoxy, or alkyl amines. The esters and amides are prepared using conventional techniques, with suitable protection of any alcohol or amino functional groups in the compound of Formula 1.

The salts of the compounds of the invention may be formed of inorganic or organic bases to form the basic salts of the free carboxyl groups or may be formed from organic or inorganic acids to obtain the acid addition salts of free amino groups. Thus, the salts may be of inorganic bases such as sodium hydroxide, potassium hydroxide, calcium hydroxide, ammonium hydroxide, magnesium hydroxide, and the like, or of organic bases such as trimethylamine, pyridine, pyrimidine, piperidine, lysine, caffeine, and the like. The acid addition salts may be formed from inorganic acids such as hydrochloric acid, hydrobromic acid, sulfuric acid, phosphoric acid, and the like, or from organic acids such as acetic acid, propionic acid, glycolic acid, pyruvic acid, oxalic acid, malic acid, tartaric acid, citric acid, benzoic acid, cinnamic acid, mandelic acid, salicylic acid, and the like. Salts of citric acid are preferred.

The salts of the compounds of Formula 1 are formed in standard protocols by treating with the appropriate base or acid at a temperature of from about 0° C. to about 100° C., preferably at room temperature either in water alone or in combination with an inert water-miscible organic solvent such as methanol, ethanol or dioxane.

USE OF THE INVENTION COMPOUNDS FOR TARGETED DRUG DELIVERY

The invention provides a general vehicle for delivering drugs to tissues specifically based on their GST content. The leaving group, when released in the target tissue, will exert its desired effects selectively in that target tissue. In addition to cytotoxicity, the released moiety may have other regulatory features. For example, where "L" is 2,3-di-t-butyl-4-hydroxyanisole, this compound is known to induce the synthesis of GSTs in mice. Administration of the compound of Formula 2 wherein "L" is 2,3-di-t-butyl-4-hydroxyanisole, will release this moiety may result in concomitant increase in GSTs. The target cells where release will occur can be regulated by manipulating the nature of the glutathione analog portion of the molecule. It may be desirable to enhance the GST component of the tumor cells concomitantly with supplying a compounds of Formulas 1 or 2 containing a cytotoxin.

As described above and demonstrated in the examples below, the various prodrugs of the invention are selective for the various isozymes of GST whose levels may be elevated in tumor cells. By determining the profile of GST isoenzyme levels in the tumor target, and matching this with the specificity of the prodrug, maximum effectiveness against the tumor cell will be obtained and maximum selectivity for the tumor cell as opposed to normal tissue can be achieved.

The compounds of Formulas 1 or 2 are administered as pharmaceutical compositions in usual formulations such as those outlined in *Remington's Pharmaceutical Sciences,* Mack Publishing Company, Easton, Pa., latest edition. Typical formulations will include those for injection, for transdermal and transmucosal administration, and for oral administration. The formulations, depending on the intended mode, may be liquids, syrups, powders, capsules, suppositories, and the like. The compounds of the invention may be included in liposomes, or in other emulsified forms. Protocols for administration and suitable formulations are subject to optimization using standard procedures known to those in the art.

The antitumor activity of the invention compounds coupled with phosphorodiamidate mustard or other toxins can be assessed using a number of human tumor xenographs to determine tumor growth inhibition or a B16 mouse melanoma and measuring the prolongation of survival to determine the efficacy of particular compounds.

COMPOUNDS FOR ASSAY OF GST ISOENZYME ACTIVITY

An alternative use for the compounds of Formulas 1 or 2 is as reagents in assays where the moiety "N(Z)" "L", when released from the compound can be readily detected. The compounds can thus conveniently be used to monitor the extent of the GST cleavage reaction, e.g., colorimetrically. Thus, an indicator moiety, such as p-nitrophenol, which is colorless when coupled to GSH or a GSH analog but develops a color on release from the compound by GST, offers an improved method of assaying GST activity. GST isoenzyme-specific assays using compounds comprising certain GSH analogs that are substrates only for selected GST isoenzymes can be used to determine substrate specificity.

SYNTHESIS OF THE INVENTION COMPOUNDS

The compounds comprising glutathione or its analogs described above coupled to a desirable leaving group can be synthesized using means generally known in the art. Where $S^x$ is an oxidized form of S or Se, the methods illustrated below can be used, incorporating modifications which render them applicable to desired compounds of the invention.

Thus, for example, compounds of Formulas 1 or 2 wherein $S^x$ is S=O, Se=O, O=S=O or O=Se=O can be produced from the corresponding compounds wherein $S^+$ is S or Se, respectively, by oxidation with mild oxidizing agents such as peroxide or peracetate. Compounds of Formulas 1 or 2 wherein $S^x$ is S=NH, Se=NH, O=S=NH, or O=Se=NH can be obtained by treatment of the appropriate precursor, or a partially oxidized form, with chloramine T under conditions known in the art. Alternatively, the method of Whitehead, J. K. et al., *J Chem Soc* (1952) 1572–1574, may be used. Precursor compounds lacking Y—CO or $AA_C$ can be converted to the compounds of Formulas 1 or 2 by coupling the Y—CO moiety through a peptide linkage or the $AA_C$ amino acid using standard peptide coupling techniques. When S* is S or Se in reduced form in these precursors, these compounds may, similarly, be converted to compounds containing S or Se in oxidized form. Compounds of Formula 1 or 2 wherein $S^x$ is a sulfonium ion, i.e., is $S^+$; may be synthesized by treating compounds with reduced —S— with alkyl halides under suitable conditions to alkylate the sulfide. $R^3$ is alkyl (1–6C) as defined above. Preferred alkyl halides for reaction to form, ultimately, compounds of Formulas 1 or 2 in this embodiment are the iodides.

For compounds of Formula 1 or 2 wherein $S^x$ is O—C=O are obtained using as a dipeptide or tripeptide starting material analogs of glutathione wherein serine substitutes for the cysteine moiety. Where $S^x$ is NH—C=O, the corresponding amidation reaction is effected with analogs wherein 2,3-diaminopropionic acid replaces cysteine.

Preferred methods of synthesis are illustrated below. Reaction Scheme 1 shows the synthesis of a compound of Formula 1; the compound used for illustration is the urethane mustard of the oxidized (sulfone) of γ-Glu-Cys-Glu; however, analogous pathways may be used to synthesize generally the class of compounds of Formula 1.

In the illustrative scheme shown, treatment of 2-bromoethyl chloroformate with dichlorodiethylamine in the presence of triethylamine yields the urethane bromide. Reaction of glutathione with this compound at pH 9–10 gives the glutathione conjugate, which is oxidized with hydrogen peroxide and peracetic acid to yield the sulfone of Formula 1.

Reaction Scheme 1

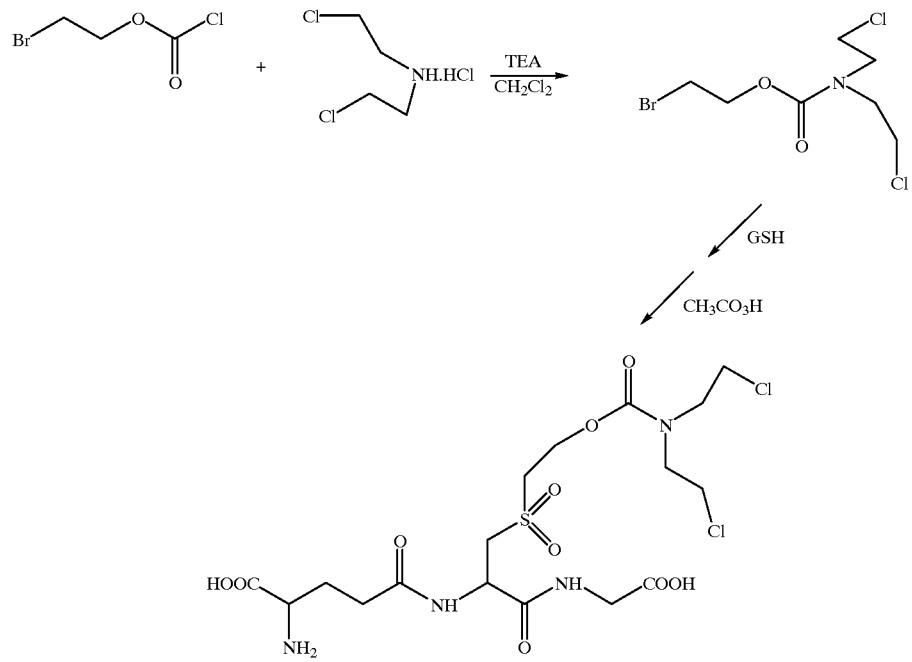

Reaction Scheme 2 shows the synthesis of an illustrative compound of Formula 2. As shown in Reaction Scheme 2, 2-bromoethyl chloroformate is reacted with phydroxymethylvaniline in triethanolamine and methylene chloride to provide the urethane bromide. The urethane bromide is then treated with POCl₃ and bis(2-chloroethyl)amine to give the tetrachloroethylphosphorodiamidate which is then treated first with glutathione or the relevant glutathione analog and then oxidized with peracetic acid to give the compound of Formula 2 as shown.

The filtrate was successively washed with 100 mL each of 2N HCl, 5% NaHCO₃, water, and brine, dried over anhydrous Na₂SO₄, filtered, and concentrated in vacuo to give 13 g of crude product as a colorless oil, which was further purified by flash column chromatography (31-X 3.7-cm of silica gel bed and eluted isocratically with dichloromethane) to give 12.5 g (85%) of the title compound as a colorless oil: Anal. (C₇H₁₂BrCl₂NO₂) C, H, N.

B. γ-Glutamyl-α-amino-β-[[2-ethoxycarbonyl-bis(2-chloreth-yl)-amine]-thio]propionylglycine

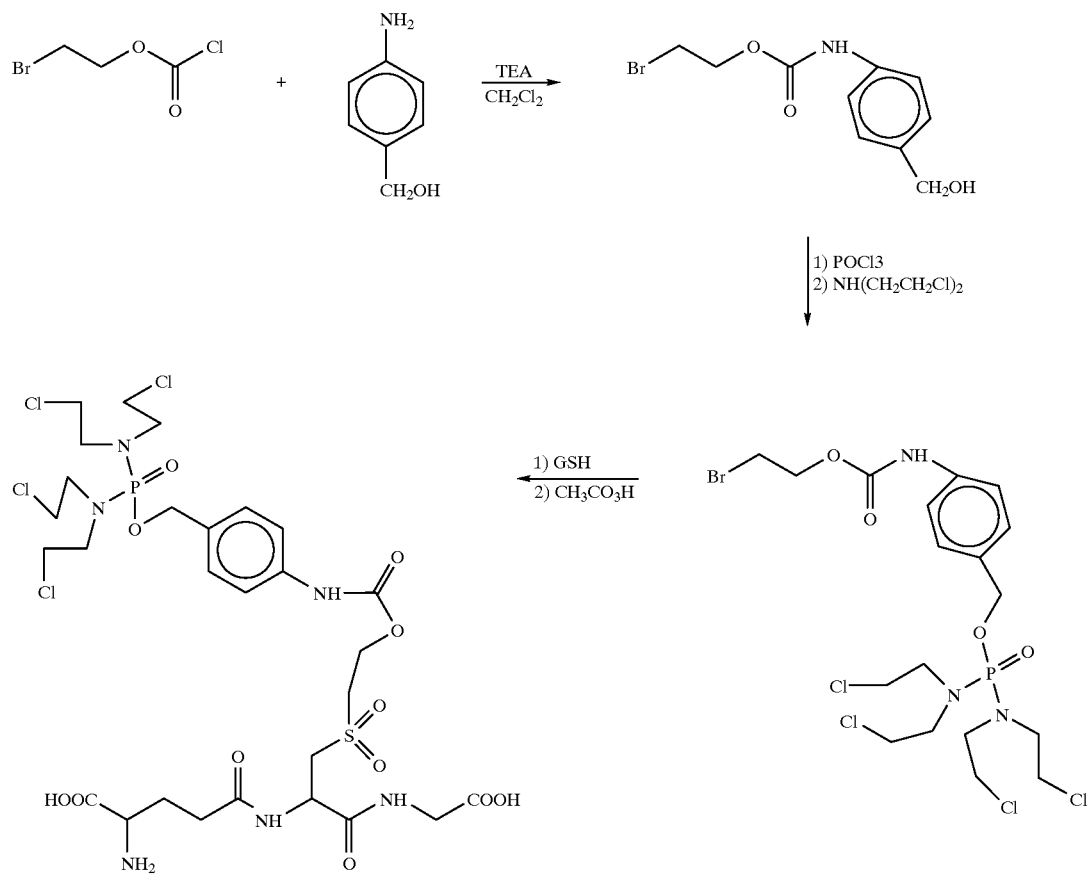

Reaction Scheme 2

The following example is intended to illustrate but not to limit the invention.

EXAMPLE 1

A Synthesis of the Diethyl Ester of the Urethane Mustard Conjugate of Oxidized γ-Glu-Cys-Gly A. 2-Bromoethoxycarbonyl[bis(2-chloroethyl)amine]

2-Bromoethyl chloroformate (5.6 mL, 50 mmol) was added to a stirred suspension of bis(2-chloroethyl)amine hydrochloride (9.8 g, 55 mmol) in 250 mL of dry dichloromethane at 0–5° C. under argon over 2 min followed by 28 mL (200 mmol) of triethylamine over 20 min. The mixture was stirred at 5–10° C. for 3 h and at room temperature for 18 h, then suction filtered. The filtrate was concentrated in vacuo.

The residue was dissolved in 200 mL ethyl acetate and suction filtered to remove the triethylamine hydrochloride.

Glutathione (6.14 g, 20 mmol) was dissolved in 100 mL water and the pH was adjusted to between 9–10 by adding 1N NaOH. To this stirred solution at room temperature was added a solution of the urethane bromide prepared in paragraph A (2.93 g, 10 mmol) in 100 mL of 1:1 ethanol/acetonitrile. The resulting clear colorless solution was stirred at room temperature under argon for 3 days. TLC of the mixture indicated completion of the reaction.

The mixture was acidified to pH 5–6 with 10% acetic acid and most of the organic solvent portion was removed in vacuo. The aqueous portion was lyophilized and purified by HPLC: (buffer A, 0.1% TFA in 1:9 acetonitrile/water; buffer B, 0.1% TFA in 9:1 acetonitrile/water); eluted by running a gradient from 0–100% buffer B at an elution rate of 12 mL/min) to give 1.7 g (33%) of the title compound as a white fluffy hygroscopic powder: mp 85–113° C. Anal. (C₁₇H₂₈Cl₂N₄O₈S.TFA.2.5 H₂O) C, H, N.

C. γ-Glutamyl-α-amino-β-[[2-ethoxycarbonyl-bis(2-chloroethyl)-amine]-sulfonyl]propionylglycine To a stirred solution of the product of paragraph B (0.519 g, 1 mmol) in 10 mL glacial acetic acid at room temperature was added 30% $H_2O_2$ (0.39 mL, 2 mmol). The reaction flask was covered with aluminum foil to exclude light and the mixture was stirred at room temperature for 4 h. The mass spectrum indicated complete conversion to sulfoxide. 0.26 mL (1.25 mmol) of 32% peracetic acid in acetic acid was added to the mixture and it was stirred at room temperature for an additional 4 h, whereupon the mass spectral analysis of the mixture indicated formation of the title compound. The mixture was lyophilized and purified by HPLC to give 0.44 g (80%) of product as a hygroscopic white fluffy powder: mp 82–93° C. Anal. $(C_{17}H_{28}Cl_2N_4O_{10}S \cdot TFA \cdot 2H_2O)$ C, H, N.

D. γ-Glutamyl-α-amino-β-[[2-ethoxycarbonyl-bis (2-chloroeth-yl)-amine]-sulfonyl]propionylglycine diethyldiester To a stirred suspension of the product of paragraph C. (0.39 g, 0.7 mmol) in 28 mL of dry ethanol in a 100 mL reaction flask fitted with a reflux condenser under argon at room temperature was added thionyl chloride (1.1 mL, 15 mmol) from the top of the condenser. The resulting clear colorless solution was stirred at gentle reflux temperature for 2.5 h. The mass spectrum indicated formation of the diethyl diester. The mixture was concentrated in vacuo and the gummy residue was purified by HPLC to give 0.17 g (40%) of the title compound as a hygroscopic fluffy white powder: mp 54–60° C. Anal. $(C_{21}H_{36}Cl_2N_4O_{10}S \cdot HCl)$ C, H, N.

We claim:

1. A compound of the formula $$\text{YCO—NHCHCO—AA}_c \quad (1)$$

with H$_2$C, S$^x$, (conj)$_n$, R$^1$, R$^2$, and —C(O)—N(Z) substituents as shown or the amides, esters or salts thereof, wherein:

$S^x$ is S=O, O=S=O, S=NH, HN=S=O, Se=O, O=Se=O, Se=NH, HN=Se=O, $S^+R^3$ wherein $R^3$ is alkyl (1–6C) or O—C=O or HN—C=O;

each R of $R^1$, and $R^2$ is independently H or a noninterfering substituent;

wherein (conj) represents a conjugated system that transmits electrons;

n is 0 or 1;

YCO is selected from the group consisting of γ-Glu, γ-Glu-Gly, Glu, Glu-Gly, βAsp, β-Asp-Gly, Asp and Asp-Gly;

$AA_C$ is an amino acid linked through a peptide bond to YCO—NCHCO— as shown; and N(Z) is a reduced nitrogen-containing leaving group.

2. The compound of claim 1 wherein each of $R^1$ and $R^2$ is independently H, substituted or unsubstituted alkyl (1–6C), substituted or unsubstituted aryl (6–12C), substituted or unsubstituted aryl alkyl (7–12C), cyano, halo, substituted or unsubstituted alkoxy (1–6C), substituted or unsubstituted aryloxy (6–12C) or substituted or unsubstituted aryl alkyloxy (7–12C).

3. The compound of claim 1 wherein N(Z) is selected from the group consisting of bis(2-chloroethyl)amine, a uracil mustard, mitomycin C, actinomycin C, vincristine, vinblastine, and dynemycin A.

4. The compound of claim 1 wherein YCO is γ-Glu.

5. The compound of claim 1 wherein $S^x$ is O=S=O.

6. The compound of claim 1 wherein $AA_C$ is glycine, phenylglycine, β-alanine, alanine or phenylalanine.

7. The compound of claim 1 wherein (conj) is para-phenylene.

8. The compound of claim 1 wherein n is 0.

9. The compound of claim 1 wherein YCO is γ-glu.

10. The compound of claim 1 wherein all of $R^1$ and $R^2$ are H.

11. The compound of claim 1 wherein $S^x$ is O=S=O.

12. The compound of claim 1 wherein $AA_C$ is selected from the group consisting of glycine, phenylglycine, β-alanine, alanine and phenylalanine.

13. The compound of claim 1 wherein N(Z) is selected from the group consisting of bis(2-chloroethyl)amine, a uracil mustard, nitomycin C, actinomycin C, vincristine, vinblastine, and dynemycin A.

14. The compounds of claim 1 wherein n is 0.

15. A pharmaceutical composition for drug delivery which composition comprises as active ingredient the compound of claim 1 in admixture with a pharmaceutically acceptable excipient.

16. A method to deliver a biologically active moiety to a target which method comprises administering to a subject containing said target the compound of claim 1 or a pharmaceutical composition thereof.

17. A compound of the formula $$\text{YCO—NHCHCO-AA}_c \quad (2)$$

with H$_2$C, S$^x$, (conj)$_n$, R$^1$, R$^2$, —C(O)—O—C(O)—NH—(conj)—C(R$^2$)—L substituents as shown or the amides, esters or salts thereof, wherein:

$S^x$ is S=O, O=S=O, S=NH, HN=S=O, Se=O, O=Se=O, Se=NH, HN=Se=O, $S^+R^3$ wherein $R^3$ is alkyl (1–6C) or O—C=O or HN—C=O;

each R of $R^1$, and $R^2$ is independently H or a noninterfering substituent;

wherein (conj) represents a conjugated system which transmits electrons;

n is 0 or 1;

YCO is selected from the group consisting of γ-Glu, γ-Glu-Gly, Glu, Glu-Gly, βAsp, β-Asp-Gly, Asp and Asp-Gly;

$AA_C$ is an amino acid linked through a peptide bond to YCO—NHCHCO— as shown; and L is an electron-withdrawing leaving group.

18. The compound of claim 17 wherein each of $R^1$ and $R^2$ is independently H, substituted or unsubstituted alkyl (1–6C), substituted or unsubstituted aryl (6–12C), substituted or unsubstituted aryl alkyl (7–12C), cyano, halo, substituted or unsubstituted alkoxy (1–6C), substituted or unsubstituted aryloxy (6–12C) or substituted or unsubstituted aryl alkyloxy (7–12C).

19. The compound of claim 17 wherein L is a phosphoroamide mustard, a phosphorodiamidate mustard, adriamycin or daunorubicin.

20. The compound of claim 17 wherein YCO is γ-Glu.

21. The compound of claim 17 wherein $S^x$ is O=S=O.

22. The compound of claim 17 wherein $AA_C$ is glycine, phenylglycine, β-alanine, alanine or phenylalanine.

23. The compound of claim 17 wherein (conj) is para-phenylene.

24. The compound of claim 17 wherein n is 0.

25. The compound of claim 17 wherein YCO is γ-glu.

26. The compound of claim 17 wherein all of $R^1$ and $R^2$ are H.

27. The compound of claim 17 wherein $S^x$ is O=S=O.

28. The compound of claim 17 wherein $AA_C$ is selected from the group consisting of glycine, phenylglycine, β-alanine, alanine and phenylalanine.

29. The compound of claim 17 wherein (conj) is para-phenylene.

30. The compound of claim 17 wherein L is a phosphoroamide mustard, a phosphorodiamidate mustard, adriamycin or daunorubicin.

31. The compound of claim 17 wherein n is 0.

32. A pharmaceutical composition for drug delivery which composition comprises as active ingredient the compound of claim 17 in admixture with a pharmaceutically acceptable excipient.

33. A method to deliver a biologically active moiety to a target which method comprises administering to a subject containing said target the compound of claim 17 or a pharmaceutical composition thereof.

* * * * *